United States Patent
Haller et al.

(10) Patent No.: US 12,352,677 B2
(45) Date of Patent: Jul. 8, 2025

(54) METHOD FOR DETERMINING A RELATIVE HUMIDITY OF THE AIR IN A MOTOR VEHICLE PASSENGER COMPARTMENT

(71) Applicant: Valeo Systemes Thermiques, Le Mesnil Saint-Denis (FR)

(72) Inventors: Régine Haller, Le Mesnil Saint-Denis (FR); Amanda Martinell, Le Mesnil Saint-Denis (FR)

(73) Assignee: Valeo Systemes Thermiques

( * ) Notice: Subject to any disclaimer, the term of this patent is extended or adjusted under 35 U.S.C. 154(b) by 334 days.

(21) Appl. No.: 17/770,150

(22) PCT Filed: Oct. 21, 2020

(86) PCT No.: PCT/FR2020/051903
§ 371 (c)(1),
(2) Date: Apr. 19, 2022

(87) PCT Pub. No.: WO2021/079064
PCT Pub. Date: Apr. 29, 2021

(65) Prior Publication Data
US 2022/0390346 A1    Dec. 8, 2022

(30) Foreign Application Priority Data
Oct. 24, 2019  (FR) ...................... 1911901

(51) Int. Cl.
*G01N 15/06* (2006.01)
*G01N 7/00* (2006.01)
(Continued)

(52) U.S. Cl.
CPC ............... *G01N 15/06* (2013.01); *G01N 7/00* (2013.01); *B60H 1/00785* (2013.01); *G01N 2015/0026* (2013.01)

(58) Field of Classification Search
CPC ...... G01N 15/06; G01N 7/00; B60H 1/00764; B60H 1/00785
See application file for complete search history.

(56) References Cited

U.S. PATENT DOCUMENTS

| 4,920,755 A | * | 5/1990 | Tadahiro | ............ B60H 1/00785 |
| | | | | 165/223 |
| 2013/0112390 A1 | * | 5/2013 | Arai | ................... B60H 1/00764 |
| | | | | 165/202 |

FOREIGN PATENT DOCUMENTS

| EP | 1588873 A1 | 10/2005 |
| FR | 3066598 A1 | 11/2018 |

(Continued)

OTHER PUBLICATIONS

International Search Report and Written Opinion in corresponding International Application No. PCT/FR2020/051903, mailed Feb. 12, 2021 (11 pages).

(Continued)

*Primary Examiner* — Lam S Nguyen
(74) *Attorney, Agent, or Firm* — Osha Bergman Watanabe & Burton LLP

(57) ABSTRACT

The invention relates to a method for determining a relative humidity of the air in a motor vehicle passenger compartment, comprising the following steps: —determining a parameter reflecting a specific humidity of the air from a relative humidity (HR1) of the air and a temperature (T1) of the air in a sensor integrating at least one temperature sensor and one relative humidity sensor, —calculating the relative humidity (HR2) of the air in said passenger compartment of the motor vehicle from said parameter and a temperature (T2) of the air in the passenger compartment.

13 Claims, 2 Drawing Sheets

(51) Int. Cl.
*B60H 1/00* (2006.01)
*G01N 15/00* (2006.01)

(56) References Cited

FOREIGN PATENT DOCUMENTS

| | | |
|---|---|---|
| JP | 2012-035689 A | 2/2012 |
| JP | 2016-017889 A | 2/2016 |
| WO | 2018-211049 A1 | 11/2018 |

OTHER PUBLICATIONS

Office Action issued in counterpart Chinese Application No. 202080074489.0, dated Oct. 25, 2023 (10 pages).
First Examination Report in corresponding Indian Application No. 202247023146, dated Jul. 26, 2022 (6 pages).
Office Action issued in counterpart Korean Patent Application No. 10-2022-7013060 mailed Sep. 2, 2024 (16 pages).

\* cited by examiner

METHOD FOR DETERMINING A RELATIVE HUMIDITY OF THE AIR IN A MOTOR VEHICLE PASSENGER COMPARTMENT

TECHNICAL FIELD AND PRIOR ART

The present disclosure relates to a method for determining a relative humidity of the air in a motor vehicle passenger compartment.

Nowadays, motor vehicles are equipped with many sensors, which measure various parameters, in order to ensure that the comfort of the passengers is always improved. In particular, these sensors allow the temperature and the humidity of the air in the passenger compartment to be adjusted, as well as allowing the air that is breathed by the passengers to be decontaminated.

However, these sensors must be associated with electronic processing of the gathered data, which requires relatively complex electronic resources requiring planning in terms of their installation in the vehicle, while the spatial constraints are greater in an electric vehicle.

SUMMARY

The present disclosure improves the situation.

To this end, the aim of the invention is a method for determining a relative humidity of the air in a motor vehicle passenger compartment, comprising the following steps: determining a parameter reflecting a specific humidity of the air from a relative humidity of the air and a temperature of the air in a sensor integrating at least one temperature sensor and a relative humidity sensor, preferably a particulate matter sensor, and computing the relative humidity of the air in said passenger compartment of the motor vehicle from said parameter and a temperature of the air in the passenger compartment.

Thus, the method according to the present invention allows the particulate matter sensor, in addition to its primary function, to provide an additional function of determining the relative humidity of the air in the passenger compartment, thereby avoiding the need for an additional sensor.

According to another aspect, said parameter is related to a partial pressure of the water in the air by means of thermodynamic laws.

According to another aspect, during the step of determining the partial pressure of the water in the air, a saturated vapor pressure is determined at the temperature of the air in the particulate matter sensor using a Bertrand-Dupré thermodynamic formula, so as to deduce therefrom the value of the partial pressure of the water in the air.

According to another aspect, during the step of determining the relative humidity of the air in the passenger compartment of the vehicle, a saturated vapor pressure at the temperature of the air in the passenger compartment is determined using a Bertrand-Dupré thermodynamic formula, then the ratio of the partial pressure of the water in the air and of said saturated vapor pressure to the temperature of the air in the passenger compartment is computed.

According to another aspect, the method comprises a step of determining the temperature of the air in the passenger compartment of the motor vehicle.

According to another aspect, the temperature of the air in the passenger compartment is measured by a temperature sensor in the passenger compartment.

According to another aspect, the temperature of the air in the passenger compartment (T2) is estimated from the temperature of the air in the particulate matter sensor (T1) in accordance with the following formula: $T2=T1+\Delta$, where $\Delta$ is an experimentally determined constant.

According to another aspect, the temperature of the air in the passenger compartment is estimated from the temperature of the air in the particulate matter sensor and from a power dissipated by electronic components of an electrical circuit arranged in the particulate matter sensor.

According to another aspect, the dissipated power is either measured or known from a voltage value in said electrical circuit.

A further aim of the invention is a device for implementing the method as described above, comprising a particulate matter sensor provided with a sensor for the air temperature in said sensor and a sensor for the relative humidity of the air in said sensor.

According to another aspect, a computer program is proposed comprising instructions for implementing all or part of the method as defined above when this program is executed by a processor.

According to another aspect, a non-transitory computer-readable storage medium is proposed, on which such a program is stored.

BRIEF DESCRIPTION OF THE DRAWINGS

Further features, details and advantages will become apparent on reading the following detailed description, and on studying the appended drawings, in which.

DESCRIPTION OF THE EMBODIMENTS

The drawings and the description below contain, for the most part, elements of a certain character. Therefore, they not only can be used to better understand this disclosure, but they also contribute to its definition, if applicable.

Figure 1:
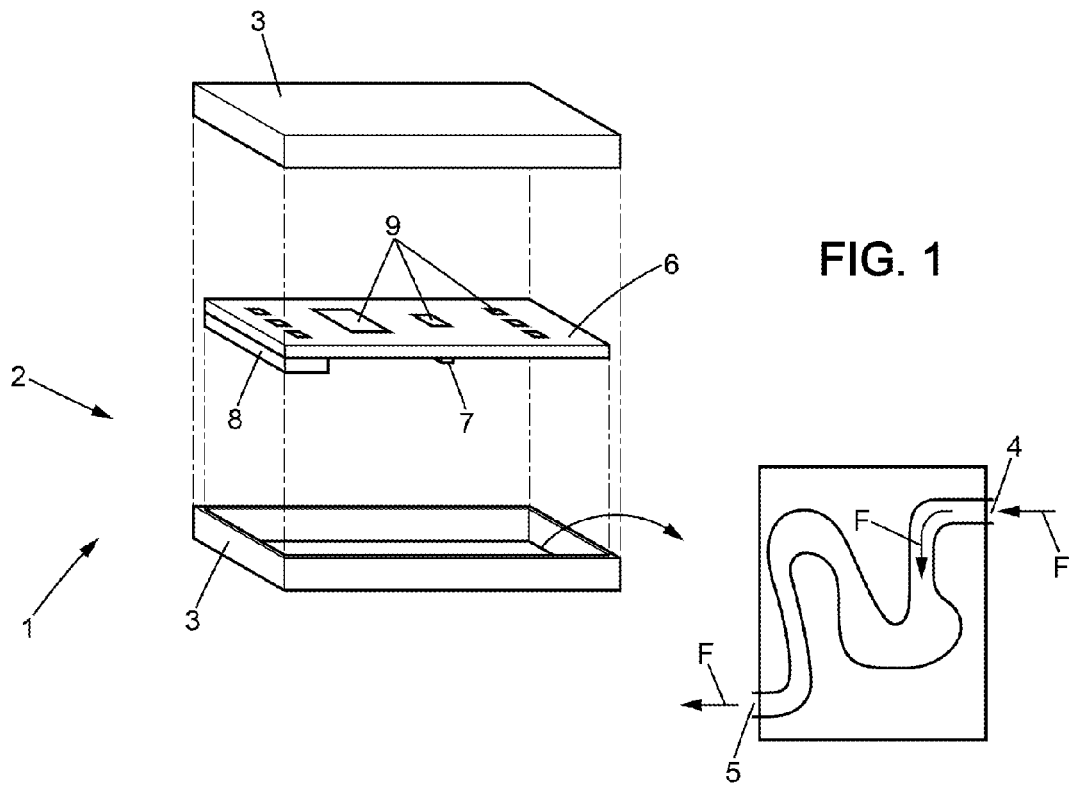
FIG. 1 partially shows a particulate matter sensor for implementing a method for determining the relative humidity of the air in a passenger compartment of a motor vehicle equipped with said sensor.

The aim of this disclosure is a method 100 for determining a relative humidity of the air, implemented by a device 1 comprising a particulate matter sensor 2, shown in FIG. 1.

The particulate matter sensor 2 preferably forms part of an air quality system of a motor vehicle for decontaminating the air intended to supply the passenger compartment of the motor vehicle. This system can be either integrated in a heating, ventilation and/or air conditioning device of the motor vehicle, or can be a specially dedicated module. In either case, the system can advantageously comprise an air purifier, such as a filter and/or ionizer, for sanitizing the air flow passing through said system before it enters the passenger compartment of the vehicle. It also can be integrated in a passenger information system using a display or a more general information system by transmitting data to computer servers (cloud) outside the car.

As shown in FIG. 1, the particulate matter sensor comprises a casing 3 defining an internal space, in which a fluid path is plotted that an air flow F takes between an air inlet 4 of the sensor 2 and an air outlet 5 of the sensor 2.

The sensor 2 also comprises optical elements (not shown) for detecting and measuring a concentration of particulate matter conveyed by the air flow F.

The term "particulate matter" is understood to mean any particle small enough to be conveyed by the air and to be inhaled. The particles can be solid, liquid, or a mixture of solids and liquids. For example, the particle diameter ranges between 0.01 μm and 10 μm. For example, the particulate matter comprises a mixture of spores, pollen, cigarette smoke, carbon, etc.

An electronic board 6 allows the optically performed measurement to be analyzed.

As can be seen from FIG. 1, the electronic board 6 particularly supports a relative humidity sensor 7 for the air flow F and a heating element 8.

The electronic board also supports other electronic components 9 forming an electrical circuit (not shown).

The particulate matter sensor 2 is advantageously configured so that, if the measured relative humidity is greater than a threshold value, then the heating element 8 is triggered, thereby ensuring that the humidity in the sensor remains low (excessively high humidity would distort the optical measurement and would risk clogging the optical sensor).

The particulate matter sensor 2 also comprises a temperature sensor for the air flow F, not shown. Preferably, the same chip measures the temperature and the relative humidity.

Throughout the remainder of the application, the temperature of the air flow F in the particulate matter sensor 2 is denoted T1 and the relative humidity of the air flow F is denoted HR1.

Throughout the remainder of the application, the temperature of the air in the passenger compartment of the vehicle is denoted T2 and the relative humidity is denoted HR2.

The method 100 will now be described with reference to FIGS. 2 to 5.

As can be seen from these figures, the method 100 comprises a step 101 of determining a parameter reflecting a specific humidity of the air from the relative humidity HR1 and the temperature T1, followed by a step 102 of computing the relative humidity of the air HR2 from said parameter and the temperature T2.

Preferably, the parameter is the partial pressure of the water in the air, denoted Pvap.

By definition, the relative humidity HR1 and the partial pressure of the water in the air Pvap are linked by the following equation:

$$P\text{vap} = HR1 * P\text{sat}(T1), \quad (1)$$

where Psat(T1) is the saturated vapor pressure at the temperature T1.

According to the method 100, the saturated vapor pressure Psat(Tl) is determined from the following formula, called Dupré-Bertrand formula:

$$\ln\left(\frac{Psat(T1)}{Po}\right) = 40.164 - \frac{64354.7}{T1} - 3.868\ln T1, \quad (2)$$

where Po is the atmospheric pressure.

However, other thermodynamic formulas available in scientific literature connecting the temperature and the saturated vapor pressure can be used. For example, the Duperray formula also can be used. Tables also can be used. The Dupré-Bertrand formula has the advantage of being particularly simple.

Thus, knowledge of the value of HR1 (by the measurement) and of the value of the saturated vapor pressure Psat(T1) allows the partial pressure of the water in the air to be determined in accordance with equation (1).

According to the method 100, the saturated vapor pressure Psat(T2) is determined from the Dupré-Bertrand formula:

$$\ln\left(\frac{Psat(T2)}{Po}\right) = 40.164 - \frac{6435.7}{T2} - 3.868\ln T2. \quad (3)$$

According to the method 100, the relative humidity HR2 is determined once the partial pressure of the water in the air Pvap and the saturated vapor pressure at temperature T2, Psat(T2) are known:

$$HR2 = \frac{Pvap}{Psat(T2)}. \quad (4)$$

Thus, by virtue of the particulate matter sensor 2 it is possible to find the value of the relative humidity in the passenger compartment HR2, which avoids having to equip the passenger compartment with a dedicated humidity sensor.

As can be seen from FIGS. 2 to 5, the method 100 also comprises a step 103 of determining the temperature T2.

Figure 2:
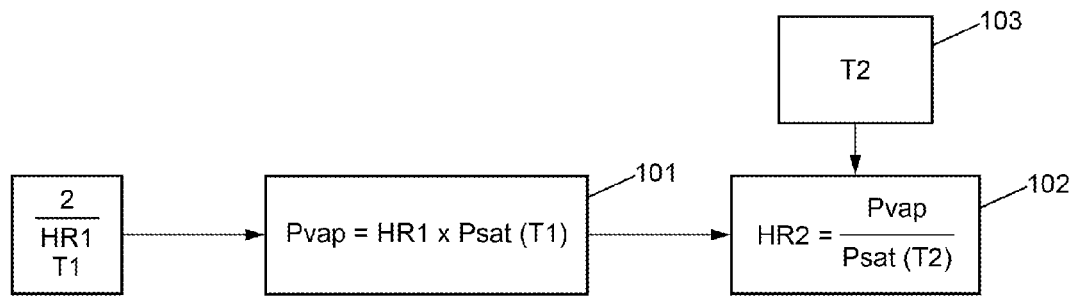
FIG. 2 shows a flow chart of the method implemented by the sensor of FIG. 1 according to a first embodiment.

According to the embodiment of FIG. 2, the temperature T2 is measured by a dedicated sensor (not shown) positioned in the passenger compartment of the vehicle.

Figure 3:
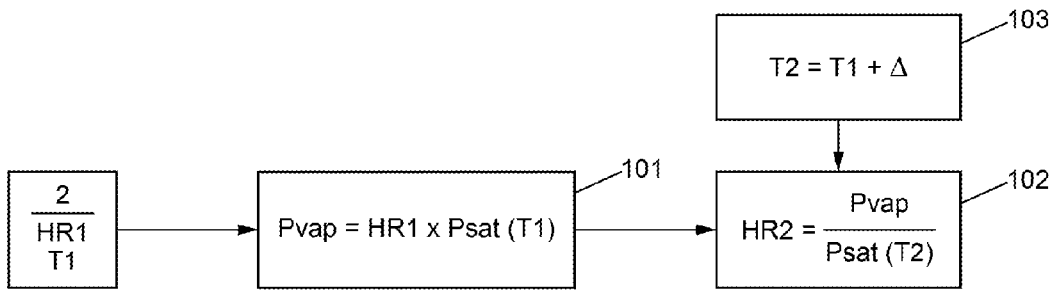
FIG. 3 shows a flow chart of the method of FIG. 1 according to a second embodiment.

According to the embodiment of FIG. 3, the temperature T2 is estimated from the temperature T1 in accordance with the following formula:

$$T2 = T1 + \Delta, \quad (5)$$

where Δ is a positive or negative constant experimentally determined, for example, during a test of measuring the temperature difference between the passenger compartment and the sensor 2.

For example, it has been experimentally determined that Δ=−12° C., according to a measurement uncertainty of 0.5° C., for a sensor PM2.5.

Figure 4:
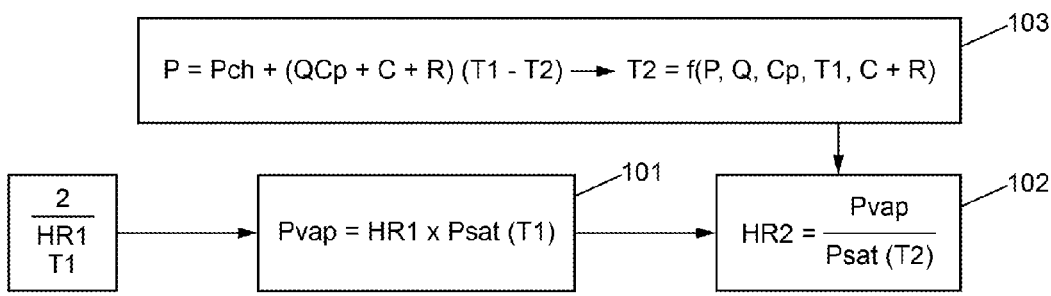
FIG. 4 shows a flow chart of the method of FIG. 1 according to a third embodiment.

According to the embodiment of FIG. 4, the temperature T2 is estimated from the temperature T1 and from a power P dissipated by the components 9 supported by the electronic board 6.

Advantageously, the power P is defined using the following equation:

$$P = QCp(T1-T2) + C(T1-T2) + R(T1-T2) + Pch, \quad (6)$$

where the parameters are as follows:

QCp(T1−T2) corresponds to the convective flow power extracted from the sensor 2 that passes through the sensor 2, with the coefficient QCp representing the product of the air flow F passing through the sensor 2 multiplied by the heat capacity;

C(T1−T2) corresponds to the heat exchange power between the inside and the outside of the sensor 2, in other words, it is the power exchanged by conduction and convection with the outside, with C representing the conductance of the casing of the sensor 2;

R(T1−T2) corresponds to a linearization of the energy radiated by the casing of the sensor 2; and Pch is the thermal power provided by the dissipation of the electronic components and by the heating element 8;

the sum of the coefficients C and R, C+R, is advantageously experimentally determined. For example, a test yielded the following values:

P ranging between 0.5 W and 1 W;

QCp ranging between 0.02 and 0.05 W/° C., for example, 0.04 W/° C.; and heating of the air T1–T2 of the order of 5° C.

In this case, the coefficient C+R is of the order of 0.2 W.

Thus, the temperature T2 is determined by equation 6 as a function of P, Q, Cp, T1, C+R.

Figure 5:
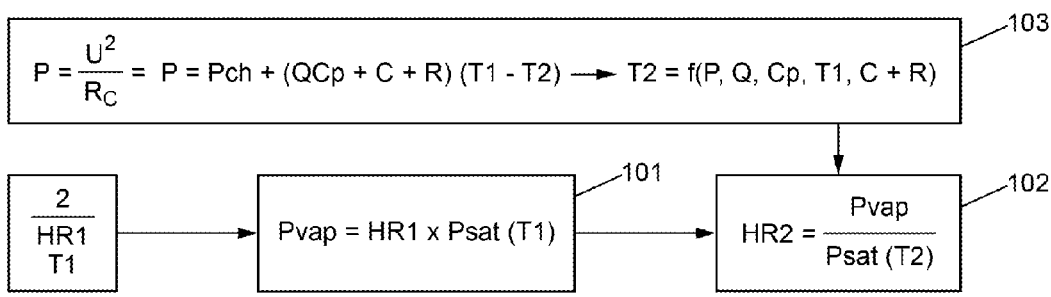
FIG. 5 shows a flow chart of the method of FIG. 1 according to a fourth embodiment.

According to the embodiment of FIG. 5, the dissipated power P is determined by means of a voltage U of the electrical circuit in accordance with the following equation:

$$P = \frac{U^2}{\text{Re}}, \quad (7)$$

where Re is the equivalent resistance of the electrical circuit.

Once the dissipated power is determined, the temperature T2 is estimated from equation 6, as explained with reference to FIG. 3.

Thus, the method 100 completely unexpectedly allows the relative humidity HR2 of the air in the passenger compartment to be determined from the particulate matter sensor 2, which limits the number of sensors that the motor vehicle must be equipped with.

It should be noted that the invention has been described in terms of its application to the particulate sensor 2. However, the invention is not limited to this type of sensor and can be applied to any sensor integrating at least one temperature sensor and a relative humidity sensor.

The invention claimed is:

1. A method for determining a relative humidity of air in a passenger compartment of a motor vehicle, comprising:
   determining a parameter that reflects a specific humidity of the air in a particulate matter sensor,
      wherein the particulate matter sensor is disposed within an air quality system of the motor vehicle in communication with an air flow through the air quality system,
      wherein the particulate matter sensor comprises at least one temperature sensor and a relative humidity sensor,
      wherein the parameter is determined using a sensor relative humidity, a sensor temperature, and a saturated vapor pressure at the sensor temperature,
      wherein the sensor relative humidity is obtained from the relative humidity sensor such that the sensor relative humidity is the relative humidity of the air in the particulate matter sensor,
      wherein the sensor temperature is obtained from the at least one temperature sensor such that the sensor temperature is a temperature of the air in the particulate matter sensor, and
      wherein the saturated vapor pressure is calculated from the sensor temperature; and
   determining a compartment relative humidity using the parameter and a compartment temperature,
      wherein the compartment relative humidity is the relative humidity of the air in the passenger compartment, and the compartment temperature is the temperature of the air in the passenger compartment.

2. The method as claimed in claim 1, wherein said parameter is a partial pressure of water in the air.

3. The method as claimed in claim 2, wherein the saturated vapor pressure is determined using a Bertrand-Dupré thermodynamic formula represented by:

$$\ln\left(\frac{Psat(T1)}{Po}\right) = 40.164 - \frac{6435.7}{T1} - 3.868\ln T1$$

where Psat is the saturated vapor pressure, T1 is the sensor temperature, and Po is an atmospheric pressure.

4. The method as claimed in claim 3,
   wherein determining the compartment relative humidity further comprises:
   determining the saturated vapor pressure at the compartment temperature using the Bertrand-Dupré thermodynamic formula, and
   determining the compartment relative humidity from a ratio of the partial pressure of the water in the air to said saturated vapor pressure at the compartment temperature.

5. The method as claimed in claim 1, further comprising: determining the compartment temperature.

6. The method as claimed in claim 5, wherein the compartment temperature is measured by a compartment temperature sensor disposed in the passenger compartment.

7. The method as claimed in claim 5, wherein the compartment temperature is estimated from the sensor temperature in accordance with the following formula: T2=T1+Δ, where Δ is an experimentally determined constant.

8. The method as claimed in claim 5, wherein the compartment temperature is estimated from the sensor temperature and from a power dissipated by electronic components of an electrical circuit arranged in the particulate matter sensor.

9. The method as claimed in claim 8, wherein the dissipated power is either measured or known from a voltage value in said electrical circuit.

10. A device for determining a relative humidity of air in a passenger compartment of a motor vehicle, the device comprising:
   a particulate matter sensor disposed within an air quality system of the motor vehicle in communication with an air flow through the air quality system, the particulate matter sensor comprising:
      at least one temperature sensor a sensor; and
      a relative humidity sensor,
   wherein the particulate matter sensor is configured to:
   determine a parameter that reflects a specific humidity of the air in the particulate matter sensor,
      wherein the parameter is determined using a sensor relative humidity, a sensor temperature, and a saturated vapor pressure at the sensor temperature,
      wherein the sensor relative humidity is obtained from the relative humidity sensor such that the sensor relative humidity is the relative humidity of the air in the particulate matter sensor,
      wherein the sensor temperature is obtained from the at least one temperature sensor such that the sensor temperature is a temperature of the air in the particulate matter sensor, and
      wherein the saturated vapor pressure is calculated from the sensor temperature; and
   determine a compartment relative humidity from the parameter and a compartment temperature, wherein the compartment relative humidity is the relative humidity of the air in the passenger compartment, and the compartment temperature is the temperature of the air in the passenger compartment.

11. The device as claimed in claim 10, wherein said parameter is a partial pressure of water in the air.

12. The device as claimed in claim 11, wherein the saturated vapor pressure is determined using a Bertrand-Dupré thermodynamic formula represented by:

$$\ln\left(\frac{Psat(T1)}{Po}\right) = 40.164 - \frac{6435.7}{T1} - 3.868 \ln T1$$

where Psat is the saturated vapor pressure, T1 is the sensor temperature, and Po is an atmospheric pressure.

13. The device as claimed in claim 12, wherein the device is further configured to:
determine the saturated vapor pressure at the compartment temperature using the Bertrand-Dupré thermodynamic formula, and
determine the compartment relative humidity from a ratio of the partial pressure of the water in the air to the saturated vapor pressure at the compartment temperature.

* * * * *